US00PP29246P3

(12) United States Plant Patent
Klemm et al.

(10) Patent No.: US PP29,246 P3
(45) Date of Patent: Apr. 17, 2018

(54) ***PELARGONIUM* PLANT NAMED 'KLEPZ15403'**

(50) Latin Name: *Pelargonium zonale*
Varietal Denomination: KLEPZ15403

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 85 days.

(21) Appl. No.: 14/998,912

(22) Filed: Mar. 2, 2016

(65) Prior Publication Data

US 2016/0360676 P1 Dec. 8, 2016

(30) Foreign Application Priority Data

Jun. 3, 2015 (CH) ..... PBR 15-3015

(51) Int. Cl.
*A01H 5/02* (2018.01)

(52) U.S. Cl.
USPC ..... Plt./325

(58) Field of Classification Search
USPC ..... Plt./325, 329
See application file for complete search history.

(56) References Cited

PUBLICATIONS

UPOV hit on *Pelargonium* plant named 'KLEPZ15403', CH PBR 15-3015, application date Jun. 3, 2015.*
UPOV hit on *Pelargonium* plant named 'KLIPZ15403', QZ PBR 44844, application date Jul. 1, 2015.*
Plant Information Sunrise TM Hot Rose+Eye Zonal Geranium, downloaded from http://www.ballseed.com/PlantInfo/?phid=028903233038071 on Jul. 20, 2017.*

* cited by examiner

*Primary Examiner* — Anne Marie Grunberg
(74) *Attorney, Agent, or Firm* — Bethany R. Roahrig; Barbara Campbell; Cochran Freund & Young LLC

(57) ABSTRACT

A new *pelargonium* plant particularly distinguished by pink purple flowers with a purple red eye, and an upright growth habit, is disclosed.

1 Drawing Sheet

Genus and species: *Pelargonium zonale*.
Variety denomination: 'KLEPZ15403'.

CROSS-REFERENCE TO RELATED APPLICATIONS

This application claims priority to and the benefit of Switzerland Plant Breeders Rights application filed on Jun. 3, 2015, Application No. 15-3015, the entire contents of which are incorporated herein by reference for all purposes.

An application with the European Community Plant Variety Office was filed on Jul. 1, 2015, File No. 2015-1526.

BACKGROUND OF THE NEW PLANT

The present invention comprises a new and distinct variety of *pelargonium*, botanically known as *Pelargonium zonale* and hereinafter referred to by the variety name 'KLEPZ15403'. 'KLEPZ15403' originated from a cross-combination in June 2010 in Stuttgart, Germany between the female *pelargonium* variety 'PZ-2006-0158' (unpatented) and the proprietary male *pelargonium* variety 'PZ-2007-0004' (unpatented).

Seeds from the cross-combination in June 2010 in Stuttgart, Germany were obtained. The seeds were sown and plants were grown for evaluation. A single plant was selected in June 2011 and subsequently named 'KLEPZ15403'. In September 2011 'KLEPZ15403' was first vegetatively propagated in Stuttgart, Germany by vegetative cuttings from stems. 'KLEPZ15403' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Pink purple flowers with a purple red eye; and
2. An upright growth habit.

DESCRIPTION OF THE PHOTOGRAPH

This new *pelargonium* plant is illustrated by the accompanying photograph which shows an overall view of the plant. The photograph is of an approximately ten-week-old plant grown in Stuttgart, Germany under greenhouse conditions in May 2014. The colors shown are as true as can be reasonably obtained by conventional photographic procedures.

DESCRIPTION OF THE NEW VARIETY

The following detailed descriptions set forth the distinctive characteristics of 'KLEPZ15403'. The data which define these characteristics were collected from asexual reproductions carried out in Stuttgart, Germany. Data was collected on plants grown 2 and a half-months after planting in Stuttgart, Germany under greenhouse conditions in June 2015. Color references are to The R.H.S. Colour Chart of The Royal Horticultural Society of London (R.H.S.), 5th edition (2007).

Classification:

*Family*.—Geraniaceae.

*Botanical*.—*Pelargonium zonale*.

*Common*.—*Pelargonium*.

*Designation*.—'KLEPZ15403'.

Parentage:

*Female parent*.—The female *pelargonium* variety 'PZ-2006-0158' (unpatented).

*Male parent*.—The proprietary male *pelargonium* variety 'PZ-2007-0004' (unpatented).

Plant:

*Form*.—Bushy and round.

*Habit*.—Upright.

*Height*.—15.0 cm to 18.0 cm.

*Spread*.—21.0 cm to 24.0 cm.

*Natural flowering season*.—Spring to autumn.

*Propagation type*.—Vegetative cuttings.

*Time to produce a finished flowering plant*.—9 to 10 weeks.

*Time to initiate and develop roots*.—18 days.

*Root description*.—White and fine, RHS 155 D.

Stems:

*Quantity of stems per plant*.—4 to 5.

*Color*.—RHS 137B and RHS 176D.

*Surface texture*.—Sparsely pubescent.

*Stem form*.—Round.

*Diameter*.—0.8 cm to 1.0 cm.

*Length*.—9.0 cm to 12.0 cm.

*Internode length*.—1.0 cm to 3.0 cm.

*Anthocyanin*.—Present, color is RHS 177B.

Leaves:

*Arrangement*.—Alternate.

*Shape*.—Kidney shaped.

*Apex*.—Obtuse, round.

*Base*.—Open.

*Margin*.—Crenate.

*Surface texture*.—Upper surface: Rough, sparsely pubescent. Lower surface: Slightly rough to smooth, sparsely pubescent.

*Length*.—5.0 cm to 7.0 cm.

*Width*.—6.0 cm to 9.0 cm.

*Color*.—Upper surface: RHS 137A. Lower surface: RHS 137C.

*Zonal area*.—Weakly present on some leaves between the center and the outer region of the leaf. Color is RHS 178A.

*Petiole*.—Length: 4.0 cm to 7.0 cm. Diameter: 0.4 cm. Color: RHS 137B. Strength: Medium.

*Venation pattern*.—Palmate.

*Venation color*.—Upper surface: RHS 137B. Lower surface: RHS 137D.

Inflorescence:

*Lastingness of flowers on the plant*.—5 days.

*Umbels*.—Quantity of umbels per plant: 4. Length: 4.0 cm to 5.0 cm. Diameter: 7.0 cm to 9.0 cm.

*Individual florets of the umbel*.—Quantity of florets per umbel: 8 to 10. Depth: 2.5 cm. Diameter: 4.0 cm.

*Fragrance*.—Absent.

Flower buds:

*Cluster shape*.—Round.

*Cluster size*.—Length: 3.5 cm. Width: 4.0 cm.

*Surface texture*.—Moderately pubescent.

*Bud*.—Height: 1.0 cm to 1.5 cm. Width: 0.7 cm. Shape: Elliptic. Apex: Peaked. Base: Blunt. Margin: Entire. Color: RHS 137C.

Petals:

*Quantity per flower*.—6 to 7 and petaloids.

*Shape*.—Drop-shaped.

*Apex*.—Round.

*Base*.—Attenuate.

*Margin*.—Entire.

*Length*.—2.5 cm.

*Width*.—1.6 cm.

*Surface texture*.—Upper surface: Smooth. Lower surface: Smooth.

*Color of lobes*.—Upper lobes: Upper surface: 1.0 cm to 2.0 cm border colored RHS N66A, eye region of approximately 1.0 cm colored RHS 61B, and center region of approximately 0.5 cm colored RHS 69C. Lower surface: RHS N74A. Lower lobes: Upper surface: 1.0 cm to 2.0 cm border colored RHS N66A, eye region of approximately 1.0 cm colored RHS 61B, and center region of approximately 0.5 cm colored RHS 69C. Lower surface: RHS N74A.

Petaloids:

*Quantity per flower*.—2 to 5.

*Shape*.—Moderate.

*Apex*.—Round.

*Base*.—Attenuate.

*Margin*.—Blunt.

*Texture* (*upper and lower surfaces*).—Smooth.

*Length*.—0.3 cm to 1.0 cm.

*Width*.—0.1 cm to 0.6 cm.

*Color*.—Upper surface: RHS N66A and RHS 69C. Lower surface: RHS N74A.

Sepals:

*Number per flower*.—5.

*Shape*.—Elliptic.

*Apex*.—Peaked.

*Base*.—Obtuse.

*Margin*.—Entire.

*Surface texture*.—Upper surface: Smooth. Lower surface: Moderately pubescent.

*Color*.—Upper surface: RHS 137D. Lower surface: RHS 137D.

*Length*.—1.1 cm.

*Width*.—0.3 cm.

Pedicel:

*Length*.—1.0 cm to 2.0 cm.

*Diameter*.—0.15 cm.

*Color*.—RHS 137D and RHS 174B.

*Surface texture*.—Moderately pubescent.

*Strength*.—Medium.

Peduncle:

*Length*.—10.0 cm to 13.0 cm.

*Diameter*.—0.5 cm.

*Color*.—RHS 137C and RHS 174B.

*Surface texture*.—Rough, moderately pubescent.

*Strength*.—Strong to medium.

Reproductive organs:

*Stamens*.—Quantity of stamens per flower: 1 to 5 (maximum). Anther length: 0.15 cm. Filament length: 0.8 cm. Filament color: RHS 49C. Pollen amount: Moderate. Pollen color: RHS N25A.

*Pistils*.—Number: 1. Stigma color: RHS 60C. Style length: 0.5 cm. Style color: RHS 60B. Ovary arrangement: Central. Ovary color: RHS 145D. Ovary diameter: 0.2 cm. Ovary length: 0.4 cm.

Fruit and seed set: None observed.

Disease and pest/insect resistance: None observed.

COMPARISON WITH PARENTAL LINES AND KNOWN VARIETY

'KLEPZ15403' is distinguished from its parents as described in Table 1:

TABLE 1

Comparison with Parental Lines

| Characteristic | 'KLEPZ15403' | Female parent 'PZ-2006-0158' | Male Parent 'PZ-2007-0004'' |
|---|---|---|---|
| Flower color | Pink purple with a purple red eye | Pink with a purple eye | Purple with an orange center |
| Zone on the leaves | Very weak | Absent | Strong |

'KLEPZ15403' can be compared to the commercial variety SUNRISE 'Evita', also known as 'KLEPZ11276' (U.S. Plant Pat. No. 24,429). Differences between the two varieties are described in Table 2:

TABLE 2

Comparison with Similar Variety

| Characteristic | 'KLEPZ15403' | Commercial line SUNRISE 'Evita' |
|---|---|---|
| Flower color | Pink purple with a purple red eye | Purple with an orange center |
| Zone on the leaves | Very weak | Strong |

We claim:

1. A new and distinct variety of *pelargonium* plant named 'KLEPZ15403' as illustrated and described herein.

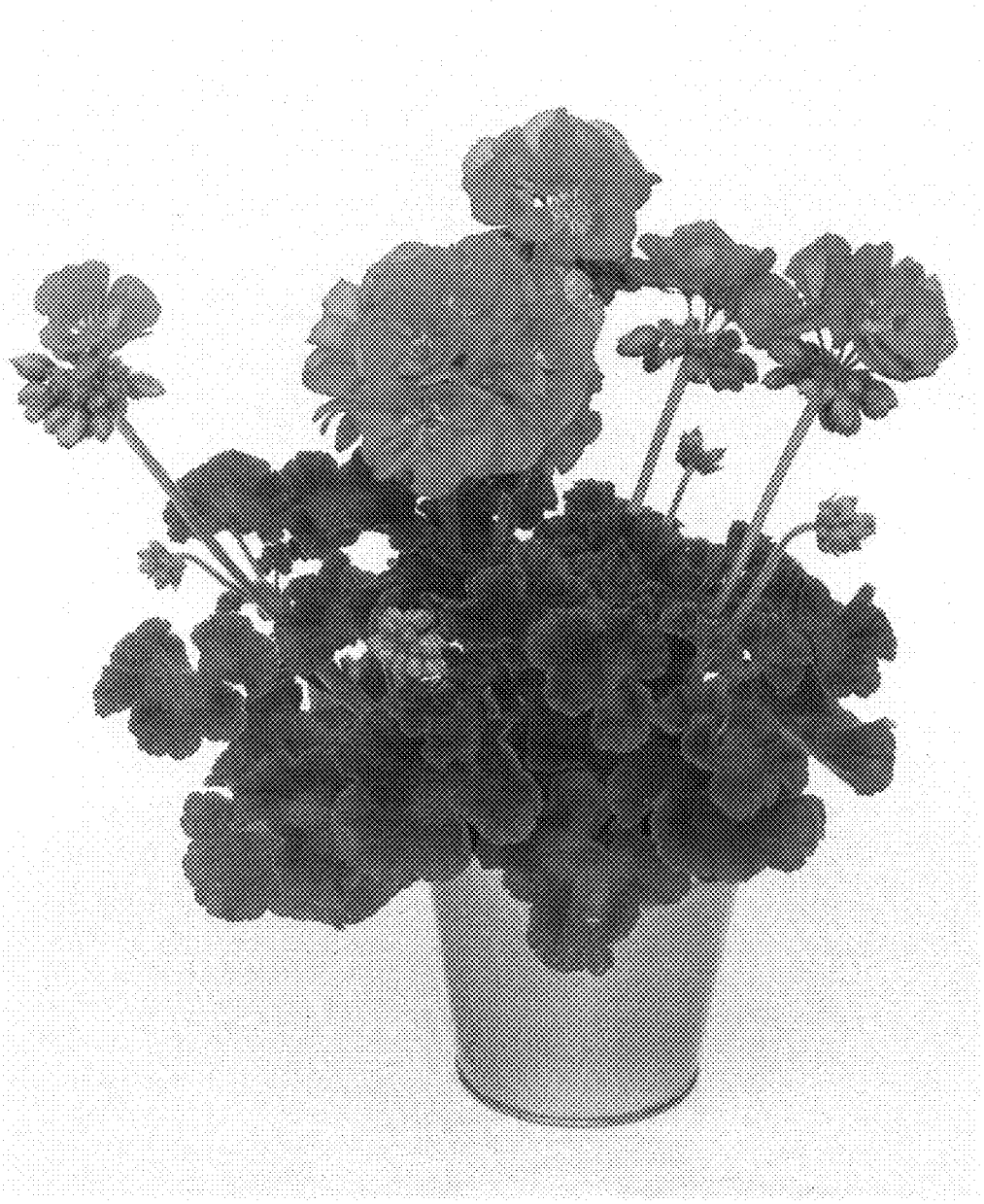

* * * * *